United States Patent
Hecker et al.

(10) Patent No.: US 12,427,102 B2
(45) Date of Patent: *Sep. 30, 2025

(54) SULFATE-FREE COSMETIC RINSE-OFF COMPOSITION COMPRISING A HYPERBRANCHED COPOLYMER

(71) Applicant: DSM IP ASSETS B.V., Heerlen (NL)

(72) Inventors: Karina Hecker, Kaiseraugst (CH); Mélanie Waeckel, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 669 days.

This patent is subject to a terminal disclaimer.

(21) Appl. No.: 17/267,921

(22) PCT Filed: Aug. 12, 2019

(86) PCT No.: PCT/EP2019/071585
§ 371 (c)(1),
(2) Date: Feb. 11, 2021

(87) PCT Pub. No.: WO2020/035447
PCT Pub. Date: Feb. 20, 2020

(65) Prior Publication Data
US 2021/0244646 A1    Aug. 12, 2021

(30) Foreign Application Priority Data
Aug. 13, 2018   (EP) .................................. 18188725

(51) Int. Cl.
*C11D 1/88*   (2006.01)
*A61K 8/73*   (2006.01)
(Continued)

(52) U.S. Cl.
CPC ............... *A61K 8/88* (2013.01); *A61K 8/731* (2013.01); *A61K 8/817* (2013.01); *A61Q 5/02* (2013.01);
(Continued)

(58) Field of Classification Search
CPC ............ C11D 1/62; C11D 3/30; C11D 3/3769
(Continued)

(56) References Cited

U.S. PATENT DOCUMENTS 9,492,366 B2 * 11/2016 Goutsis .................... A61K 8/44
2011/0182843 A1   7/2011 Derks et al.
(Continued)

FOREIGN PATENT DOCUMENTS

AU   2012/337567   6/2014
CA   2143558       8/1996
(Continued)

OTHER PUBLICATIONS

JP Application No. P2021-503536, Notice of Reasons for Rejection with English-language Translation dated Feb. 24, 2023.
(Continued)

*Primary Examiner* — Gregory R Delcotto
(74) *Attorney, Agent, or Firm* — Nixon & Vanderhye, P.C.

(57) ABSTRACT

The present invention relates to sulfate-free cosmetic rinse-off compositions which comprises a hyperbranched copolymer of the monomers dodecenyl succinic acid anhydride, diisopropanol amine and bis-dimethylamino-propyl amine having quaternary terminal groups.

23 Claims, 2 Drawing Sheets

Figure 1A:
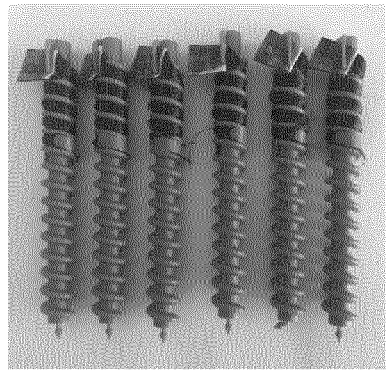

Foam development:

(51) Int. Cl.
  *A61K 8/81*  (2006.01)
  *A61K 8/88*  (2006.01)
  *A61Q 5/02*  (2006.01)
  *A61Q 19/10* (2006.01)
  *C11D 1/62*  (2006.01)
  *C11D 3/30*  (2006.01)
  *C11D 3/37*  (2006.01)

(52) U.S. Cl.
  CPC ............... *A61Q 19/10* (2013.01); *C11D 1/62* (2013.01); *C11D 3/30* (2013.01); *C11D 3/3769* (2013.01); *A61K 2800/30* (2013.01); *A61K 2800/544* (2013.01)

(58) Field of Classification Search
  USPC ................................ 510/119, 123, 475, 504
  See application file for complete search history.

(56) References Cited

U.S. PATENT DOCUMENTS

| | | |
|---|---|---|
| 2014/0348771 A1 | 11/2014 | Beumer et al. |
| 2014/0360946 A1 | 12/2014 | Arts et al. |
| 2015/0216789 A1 | 8/2015  | Daenen et al. |
| 2015/0320670 A1 | 11/2015 | Daenen et al. |
| 2017/0071836 A1 | 3/2017  | Schelges et al. |
| 2018/0098923 A1 | 4/2018  | Hutton, III |

FOREIGN PATENT DOCUMENTS

| | | | |
|---|---|---|---|
| EP | 2883533 A1 * | 6/2015  | ............ A61K 8/342 |
| EP | 2 794 729    | 4/2016  | |
| GB | 2547064      | 8/2017  | |
| JP | 2-129296     | 5/1990  | |
| JP | 3-68509      | 3/1991  | |
| JP | 7-48234      | 2/1995  | |
| JP | 2008-517007  | 5/2008  | |
| JP | 2009-528391  | 8/2009  | |
| JP | 2010-516801  | 5/2010  | |
| JP | 2010-275198  | 12/2010 | |
| JP | 2014-533683  | 12/2014 | |
| JP | 2015-529674  | 10/2015 | |
| JP | 2021-533092  | 12/2021 | |
| KR | 2015-0056549 | 5/2015  | |
| WO | 2014/041019  | 3/2014  | |
| WO | 2017106276 A1| 6/2017  | |
| WO | WO 2017/112586 | 6/2017 | |

OTHER PUBLICATIONS

International Search Report for PCT/EP2019/071585 mailed Oct. 30, 2019, 4 pages.
Written Opinion of the ISA for PCT/EP2019/071585 mailed Oct. 30, 2019, 7 pages.
"Research disclosure", vol. 606, No. 33, Oct. 1, 2014, 6 pages.
Final Rejection, JP Application No. P2021-503536, Nov. 28, 2023.

* cited by examiner

Preparation of Curls:

Curl definition:

*Ref.1*  *Ref.2*

1  2  3  4

Foam development:

Foam decay:

SULFATE-FREE COSMETIC RINSE-OFF COMPOSITION COMPRISING A HYPERBRANCHED COPOLYMER

This application is the U.S. national phase of International Application No. PCT/EP2019/071585 filed Aug. 12, 2019 which designated the U.S. and claims priority to EP patent application Ser. No. 18/188,725.8 filed Aug. 13, 2018, the entire contents of each of which are hereby incorporated by reference.

TECHNICAL FIELD

The present invention relates to the field of cosmetics, particularly to field of hair care.

BACKGROUND OF THE INVENTION

Cosmetic rinse-off compositions currently use sulfates as usual ingredients. Sulfates are an important chemical class of anionic surfactants. Due to their excellent cleansing and foaming properties they are particularly used in cosmetic rinse-off compositions. In addition, viscosity adjustment with salt is possible as a very cost-efficient methodology when sulfates are used as main surfactants. However, for a variety of reasons, such as skin-irritation customers increasingly demand sulfate-free cosmetic products.

Sulfate-free shampoos/cleansing formulations in the market are mainly based on alkylpolyglucosides (APG) and betaines, which are found not to foam as well as sulfated surfactants. Several approaches have been proposed to overcome this issue.

CA 2143558 A1 discloses a sulfate-free shampoo composition comprising alkylamido betaine, alkanolamide and sarcosinates.

GB 2547064 A discloses cleansing products comprising biosurfactants, C10-C20 acyl lactylates and less than 0.5 wt.-% of sulphated surfactants.

The main disadvantage of the alternative approaches are difficulties to adjust the viscosity of the final product in a cost saving manner as well as the chemical instability of these alternative surfactants, finally resulting in decreasing of viscosities of those formulations as well as in losing the foaming properties after longer time.

"Frizzy" hair is a major hair care problem for consumers, particularly those with coarse, wavy or curly hair, as well as for consumers who have hair which is stressed due to frequently chemical, mechanical or hot iron treatments. Frizzy hair is characterized by a multiplicity of fly-away strands, which gives the total style an unruly look. Frizzy hair is difficult to manage during styling, and it tends to lose its natural shape and/or its curl definition This is a no go for most consumers who desire good style and style retention all day long.

SUMMARY OF THE INVENTION

Thus, there is an ongoing need for a sulfate-free cosmetic rinse-off composition which exhibits excellent foaming properties and, therefore, enables a good cleaning of the hair and/or skin.

It has now surprisingly been found that a composition comprising a specific hyperbranched copolymer of the monomers (i) and (ii) and (iii) is able to solve this problem. This is particularly surprising as said hyperbranched copolymer has no sulfate groups.

It has, furthermore, been found that said hyperbranched copolymer also leads to significant lower combing force.

Further aspects of the invention are subject of further independent claims. Particularly preferred embodiments are subject of dependent claims.

DETAILED DESCRIPTION OF THE INVENTION

In a first aspect the present invention relates to a sulfate-free cosmetic rinse-off composition comprising a hyperbranched copolymer of the monomers
 (i) dodecenyl succinic acid anhydride
 (ii) diisopropanol amine
 (iii) bis-dimethylaminopropyl amine
having terminal groups of formula

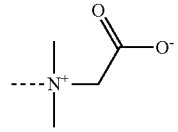

and having a molecular weight Mn of between 1200 and 4000 g/mol;
wherein the sulfate-free cosmetic rinse-off composition comprises less than 0.5% by weight, particularly less than 0.1% by weight, more particularly less than 0.05% by weight, relative to the weight of the composition, of any anionic surfactant having a terminal anionic group of the formula

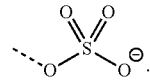

The term "rinse-off", as contrasted with the term "leave-on", is used in the present document to mean that the compositions of the present invention are used in a context whereby the composition is ultimately rinsed or washed from the hair or skin either after or during the application of the product. A "leave-on" product, refers to a composition that is applied to the hair or skin and not further subjected to a rinsing step.

The term "molecular weight Mn" stands for the number average molecular weight (regularly called also number average molar mass).

The term "free" as used in the present document, for example in "sulfate-free", is used to mean that the respective substance is only present at amounts of less than 0.5% by weight, particularly less than 0.1% by weight, more particularly less than 0.05% by weight, relative to the weight of the composition. Preferably, "free" means that the respective substance is completely absent in the composition.

The term "sulfate-free" is used in the present document to mean that the composition is free of any anionic surfactant having a terminal anionic group of the formula

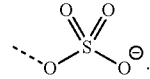

Hence, the sulfate-free cosmetic rinse-off composition is particularly free of sulfates of the group consisting of alkyl sulfates, alkyl ether sulfates, alkyl amido ether sulfates, alkylaryl polyether sulfates and monoglycerides sulfate as well as mixtures thereof.

Particularly the sulfate-free cosmetic rinse-off composition is particularly free of sulfates selected the group consisting of ammonium C12-15 alkyl sulfate, ammonium C12-16 alkyl sulfate, ammonium capryleth sulfate, ammonium cocomonoglyceride sulfate, ammonium coco-sulfate, ammonium C12-15 pareth sulfate, ammonium dimethicone PEG-7 sulfate, ammonium laureth sulfate, ammonium laureth-5 sulfate, ammonium laureth-7 sulfate, ammonium laureth-9 sulfate, ammonium laureth-12 sulfate, ammonium lauryl sulfate, ammonium myreth sulfate, ammonium myristyl sulfate, ammonium nonoxynol-4 sulfate, ammonium nonoxynol-30 sulfate, ammonium sulfate, arginine laureth sulfate, arginine PEG-4 cocamide sulfate, DEA-C12-13 alkyl sulfate, DEA-C12-15 alkyl sulfate, DEA-Cetyl sulfate, DEA-C12-13 pareth-3 sulfate, DEA-laureth sulfate, DEA-lauryl sulfate, DEA-myreth sulfate, DEA-myristyl sulfate, diethylamine laureth sulfate, dimethicone PEG-7 sulfate, magnesium coceth sulfate, magnesium coco-sulfate, magnesium laureth sulfate, magnesium laureth-5 sulfate, magnesium laureth-8 sulfate, magnesium laureth-16 sulfate, magnesium lauryl sulfate, magnesium myreth sulfate, magnesium oleth sulfate, magnesium PEG-3 cocamide sulfate, magnesium sulfate, magnesium/TEA-coco-sulfate, manganese sulfate, MEA-laureth sulfate, MEA-lauryl sulfate, MIPA C12-15 pareth sulfate, MIPAlaureth sulfate, MIPA-lauryl sulfate, sodium C8-10 alkyl sulfate, sodium C10-16 alkyl sulfate, sodium C11-15 alkyl sulfate, sodium C12-13 alkyl sulfate, sodium C12-15 alkyl sulfate, sodium C12-18 alkyl sulfate, sodium C16-20 alkyl sulfate, sodium coceth sulfate, sodium coceth-30 sulfate, sodium coco/babassu/andiroba sulfate, sodium coco/babassu sulfate, sodium coco/hydrogenated tallow sulfate, sodium cocomonoglyceride sulfate, sodium coco-sulfate, sodium C9-15 pareth-3 sulfate, sodium C10-15 pareth sulfate, sodium C10-16 pareth-2 sulfate, sodium C12-13 pareth sulfate, sodium C12-14 pareth-3 sulfate, sodium C12-15 pareth sulfate, sodium C12-15 pareth-3 sulfate, sodium C13-15 pareth-3 sulfate, sodium C12-14 Sec-pareth-3 sulfate, sodium deceth sulfate, sodium decyl sulfate, sodium dermatan sulfate, sodium dextran sulfate, sodium dodoxynol-40 sulfate, sodium ethylhexyl sulfate, sodium laneth sulfate, sodium laureth sulfate, sodium laureth-5 sulfate, sodium laureth-7 sulfate, sodium laureth-8 sulfate, sodium laureth-12 sulfate, sodium laureth-40 sulfate, sodium lauryl hydroxyacetamide sulfate, sodium lauryl sulfate, sodium/MEA-PEG-3 cocamide sulfate, sodium myreth sulfate, sodium myristyl sulfate, sodium nonoxynol-1 sulfate, sodium nonoxynol-3 sulfate, sodium nonoxynol-4 sulfate, sodium nonoxynol-6 sulfate, sodium nonoxynol-8 sulfate, sodium nonoxynol-10 sulfate, sodium nonoxynol-25 sulfate, sodium octoxynol-2 sulfate, sodium octoxynol-6 sulfate, sodium octoxynol-9 sulfate, sodium oleth sulfate, sodium oleyl sulfate, sodium palmitoyl chondroitin sulfate, sodium PEG-4 cocamide sulfate, sodium PEG-4 lauramide sulfate, sodium PPG-16/PEG-2 lauryl ether sulfate, sodium tallow sulfate, sodium/TEA C12-13 pareth-3 sulfate, TEA-C10-15 alkyl sulfate, TEA-C11-15 alkyl sulfate, TEA-C12-13 alkyl sulfate, TEA-C12-14 alkyl sulfate, TEA-C12-15 alkyl sulfate, TEA-coco-sulfate, TEA-C11-15 pareth sulfate, TEA-C12-13 pareth-3 sulfate, TEALaneth-5 sulfate, TEA-laureth sulfate, TEA-lauryl sulfate, TEA-Oleyl sulfate, TEAPEG-3 cocamide sulfate, TEA-sulfate, TIPA-laureth sulfate and TIPA-lauryl sulfate as well as mixtures thereof.

The sulfate-free cosmetic rinse-off composition comprises a hyperbranched copolymer of the monomers
(i) dodecenyl succinic acid anhydride
(ii) diisopropanol amine
(iii) bis-dimethylaminopropyl amine
having terminal groups of formula

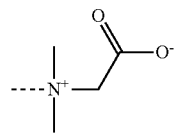

and having a molecular weight Mn of between 1200 and 4000 g/mol.

Said hyperbranched copolymer is preferably prepared by the following steps:
a1) polymerizing the monomers (i) and (ii) and (iii) to yield a polyesteramide having terminal dimethyl amino groups of the formula

a2) quaternization of the dimethyl amino groups of the polyesteramide of step a1) by 2-chloroacetate, particularly by sodium 2-chloroacetate.

Details for the polymerization step a1) to yield the respective polyesteramide having terminal dimethyl amino groups of the formula

are disclosed for example by EP 2 794 729 B1.

Preferably in the polymerization step a1) the monomer (iii) is added to a mixture of monomers (ii) and (iii) under stirring, followed by heating.

Details of the quaternization step a2) are disclosed as well by EP 2 794 729 B1. Therefore, the entire content of EP 2 794 729 B1 is hereby incorporated by reference.

The amount of the hyperbranched copolymer of the monomers
(i) dodecenyl succinic acid anhydride
(ii) diisopropanol amine
(iii) bis-dimethylaminopropyl amine
having terminal groups of formula

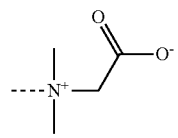

and having a molecular weight Mn of between 1200 and 4000 g/mol is typically between 0.1 and 2% by weight, relative the weight of the sulfate-free cosmetic rinse-off composition.

It is preferred that the molar ratio of the monomers (i) to (ii) is between 5:1 and 0.5:1, particularly between 4:1 and 1:1, preferably between 3:1 and 3:2.

It is further preferred that the molar ratio of the monomers (i) to (iii) is between 5:1 and 0.5:1, particularly between 3:1 and 1:1, preferably between 2.5:1 and 1.1:1.

The hyperbranched copolymer has preferably a number average molecular weight $M_n$ of between 1400 and 3000 g/mol, preferably between 2100 and 2400 g/mol, more preferably between 2100 and 2300 g/mol.

Preferably, the hyperbranched polymer is polyquaternium-110, also identified by CAS Number 1323977-82-7.

In a preferred embodiment the sulfate-free cosmetic rinse-off composition further comprises at least one cationic polymer having quaternary ammonium groups.

In a first preferred embodiment these cationic polymers having quaternary ammonium groups are
either a homopolymer (P1) of

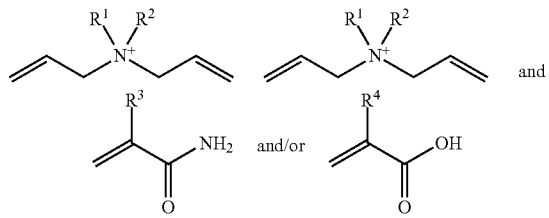

and or a copolymer (P2) of
wherein
$R^1$ and $R^2$ represent independently from each other either a linear or a branched $C_{1-10}$-alkyl group, particularly a linear or branched $C_{1-3}$-alkyl group; and
$R^3$ and $R^4$ represent independently from each other either H or a methyl group.

The homopolymers (P1) and copolymers (P2) are particularly selected from the group consisting of polyquaternium-6, polyquaternium-7, polyquaternium-22 and polyquaternium-39, preferably is polyquaternium-6.

In a second preferred embodiment these cationic polymers having quarternary ammonium groups are copolymers of vinylpyrrolidone having quarternary ammonium groups. They are particularly selected from the group consisting of polyquaternium-11, polyquaternium-16, polyquaternium-28, polyquaternium-44, polyquaternium-46, polyquaternium-68 and polyquaternium-87.

In a third preferred embodiment these cationic polymers having quaternary ammonium groups are hydroxyethyl cellulose derived polymers having quarternary ammonium groups. They are particularly selected from the group consisting of polyquaternium-4, polyquaternium-10, polyquaternium-24 and polyquaternium-67.

It is preferred that the sulfate-free cosmetic rinse-off compositions are cleansing compositions, such as in particular of the group consisting of sulfate-free shampoos, shower gels, bubble bath, shower oils, shower emulsions, shower lotions, liquids soaps, handwashing lotions, phase wash lotions, syndets and soaps.

More preferably the sulfate-free cosmetic rinse-off compositions are compositions selected from the group consisting of sulfate-free liquid soaps, soaps, syndets and shampoos.

Most preferably, the sulfate-free cosmetic rinse-off composition is a sulfate free shampoo composition.

The sulfate-free cosmetic rinse-off compositions can contain further ingredients usually employed in the preparation of such compositions. Such ingredients are well known by the person skilled in the art and will be selected depending on the type of use envisaged.

Particularly, the sulfate-free cosmetic rinse-off composition comprises water. The amount of water depends strongly on the type of application and use of the composition. In case of a shampoo the amount of water is typically selected in the range of 50 to 90% by weight, relative to the weight of the rinse-off composition. In case of body-washing gels, cremes and lotions the amount of water is typically in the range of 30-90% by weight, relative to the weight of the rinse-off composition. In the case of soaps and syndets, the amount of water is typically in the range of 5-40% by weight, relative to the weight of the rinse-off composition.

Particularly, the sulfate-free cosmetic rinse-off may comprise further sulfate-free surfactants, such as cationic, anionic, non-ionic or amphoteric surfactants. Examples of suitable anionic surfactants are the alkanoyl isothionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium or mono-, di- or triethanolamine salts. The alkyl and acyl groups generally contain from 8 to 18, preferably from 10 to 16, carbon atoms and may be unsaturated, alkyl ether sulphosuccinates, alkyl ether phosphates and alkyl ether carboxylic acids and salts thereof may contain from 1 to 20 ethylene oxide or propylene oxide units per molecule.

In particular, the anionic surfactants are selected from sodium oleyl succinate, ammonium lauryl sulphosuccinate, sodium lauryl ether sulphosuccinate, sodium cocoyl isethionate, sodium lauryl isethionate, lauryl ether carboxylic acid and sodium N-lauryl sarcosinate or mixtures thereof. Preferred anionic surfactants are sodium lauryl ether sulphosuccinate (n) EO, (where n is from 1 to 4, in particular n is 3).

The total amount of the anionic surfactant(s) in the shampoo preparations according to the present invention is preferably selected in the range of 0.1 to 25 wt.-%, more preferably in the range of 5 to 20 wt.-%, most preferably in the range of 2 to 15 wt.-%, based on the total weight of the shampoo preparation.

Examples of nonionic surfactants include condensation products of aliphatic (C8-C18) primary or secondary linear or branched chain alcohols with alkylene oxides, usually ethylene oxide and generally having from 6 to 30 ethylene oxide groups. Other representative nonionic surfactants include mono- or di-alkyl alkanolamides such as e.g. coco mono- or di-ethanolamide and coco mono-isopropanolamide. Further nonionic surfactants which can be included in the sulfate-free cosmetic rinse-off composition are the alkyl polyglycosides (APGs). Typically, the APG is one which comprises an alkyl group connected (optionally via a bridging group) to a block of one or more glycosyl groups such as e.g. Oramix™ NS 10 ex Seppic; PLANTACARE® 818UP, PLANTACARE® 1200 and PLANTACARE® 2000 ex BASF. Typically, non-ionic surfactants are used in an amount ranging from 0.5 to 10 wt.-%, preferably from 2 to 8 wt.-% based on the total weight of the sulfate-free cosmetic rinse-off composition.

Examples of amphoteric (or zwitterionic) surfactants are alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in the rinse-off compositions include lauryl amine oxide, cocodimethyl sulphopropyl betaine, lauryl betaine, cocamidopropyl betaine (CAPB), sodium cocoamphoacetate and disodium cocoamphodiacetate. Particularly preferred amphoteric or zwitterionic surfactants which can be used in the rinse-off composition are cocamidopropyl betaine, cocoamphoacetate or cocoamphodiacetate such as most preferably sodium cocoamphoacetate.

Mixtures of any of the foregoing amphoteric or zwitterionic surfactants may also be suitable. Preferred mixtures are those of cocamidopropyl betaine with further amphoteric or zwitterionic surfactants as described above such as in particular with sodium cocoamphoacetate or disodium cocoamphodiacetate.

Typically, the amphoteric or zwitterionic surfactants can be included in an amount ranging from 0.5 to about 8 wt.-%, preferably from 1 to 5 wt.-% based on the total weight of the sulfate-free cosmetic rinse-off composition.

The sulfate-free cosmetic rinse-off composition may contain further ingredients to enhance the performance and/or consumer acceptability such as antioxidants, thickeners, softeners, antifoaming agents, moisturizers, fragrances, co-surfactants, fillers, sequestering agents, cationic-, nonionic- or amphoteric polymers or mixtures thereof, acidifying or basifying agents, dyes, colorants, pigments or nanopigments, pearlizers or opacifiers, organic or inorganic particles, viscosity modifiers, and natural hair nutrients such as botanicals, fruit extracts, sugar derivatives and/or amino acids or any other ingredients usually formulated into rinse off compositions. The necessary amounts of the adjuvants and additives can, based on the desired product, easily be chosen by a person skilled in the art in this field and will be illustrated in the examples, without being limited hereto.

The rinse-off composition may further comprise a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the sulfate-free cosmetic rinse-off composition. Polyacrylic acid is available commercially as Carbopol® 420, Carbopol® 488 or Carbopol® 493. Polymers of acrylic acid cross-linked with a polyfunctional agent may also be used; they are available commercially as Carbopol® 910, Carbopol® 934, Carbopol® 941, Carbopol® 980 and Carbopol® Ultrez 10 Polymer. Examples of suitable copolymers of a carboxylic acid containing monomer and acrylic acid esters are Carbopol® 1342, Carbopol® Ultrez 20 or Carbopol® Ultrez 21, Pemulen TR1 or Pemulen TR2. All Carbopol® or Pemulen® materials are available from Lubrizol.

A suitable heteropolysaccharide gum is xanthan gum, for example Keltrol®-types or Kelzan®-types from Kelco, Vanzan NF from RT Vanderbilt Inc. or Rhodicare®-types from Rhodia.

Mixtures of any of the above suspending agents may be used. Preferred is a mixture of cross-linked polymer of acrylic acid and crystalline long chain acyl derivative.

The suspending agent(s) will generally be used at levels of from 0.1 to 10 wt.-%, preferably from 0.5 to 6 wt.-%, more preferably from 0.9 to 4 wt.-%, based on the total weight of the rinse-off composition.

Customary film formers include, for example, chitosan, microcrystalline chitosan, quaternized chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

The viscosity of the sulfate-free cosmetic rinse-off composition, particularly rinse-off shampoo composition, is preferably selected in the range of 500 and about 20000 mPa·s at 20° C., preferably 1000 to 10000, in particular 1000 to 7000 mPa·s at 20° C., measured with Brookfield or Hoppler viscosimeters at a shear rate of 10 sec-1. The viscosity of the shampoo compositions can be adjusted with known viscosity enhancers (thickeners). Preferred viscosity enhancers are PEG-55 propyleneglycol oleate and PEG-18 glyceryl oleate/cocoate known with the trade names Antil® 141 and 171, respectively and PEG-160 sorbitan triisostearate known with a trade name RHEODOL TW-IS399C such as most preferably PEG-18 glyceryl oleate/cocoate. It should be noted that in the case that a preparation is delivered in the form of a foam from a pump-foamer and/or aerosol can, those compositions should not be thickened and have a viscosity value not more than 500 mPa·s, more preferably 250 mPa's measured as mentioned above at 20° C.

The sulfate-free cosmetic rinse-off composition as described above in great detail is preferably also silicone-free, i.e. it is preferably free of any silicone oils and/or silicone surfactants.

Furthermore, the sulfate-free cosmetic rinse-off composition is preferably free of mineral oil and is petroleum free.

In an even more preferred embodiment, the sulfate-free cosmetic rinse-off composition is also free of parabenes.

In the most preferred embodiment, the sulfate-free cosmetic rinse-off composition is free of any silicone oils and/or silicone surfactants and of any mineral oil and of petroleum as well as of any parabenes.

In a further aspect, the present invention relates to the use of a hyperbranched copolymer of the monomers
(i) dodecenyl succinic acid anhydride
(ii) diisopropanol amine
(iii) bis-dimethylaminopropyl amine
having terminal groups of formula

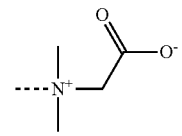

and having a molecular weight Mn of between 1200 and 4000 g/mol in a sulfate-free cosmetic rinse-off composition for increasing the foaming of said composition upon application on hair or skin.

It has been found that the sulfate-free cosmetic rinse-off compositions have an excellent foaming behavior, despite the absence of sulfates.

It has been found that the sulfate-free cosmetic rinse-off compositions have a significant better foaming development as compared to the respective compositions where the above mentioned hyperbranched copolymer of the monomers (i), (ii) and (iii) is not present. This relates to a faster foam development as well as to a higher maximum foam volume. Furthermore, the foam of the sulfate-free cosmetic rinse-off compositions is shown to be very stable and the decay of foam is significantly less than the one which is produced by the respective compositions where the above mentioned hyperbranched copolymer of the monomers (i), (ii) and (iii) is not present.

Due to the absence of sulfates the sulfate-free cosmetic rinse-off composition as mentioned above have significant advantages, particularly in reduced skin irritation as compared to the respective compositions comprising sulfates.

In an even further aspect, the present invention relates to the use of a hyperbranched copolymer of the monomers
(i) dodecenyl succinic acid anhydride
(ii) diisopropanol amine
(iii) bis-dimethylaminopropyl amine
having terminal groups of formula

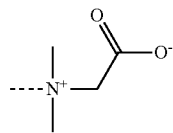

and having a molecular weight Mn of between 1200 and 4000 g/mol in a sulfate-free shampoo for decreasing combing force when combing hair which is treated with sulfate-free shampoo.

It has been observed that the combing properties are remarkably improved. Particularly, it has been found that the combing force is strongly reduced. It has been observed that the combing force is significantly reduced for both wet and dry hair. Particularly, significant reduction is observed when the combing is performed as long as the hair is in wet conditions.

It is particularly observed that the surface of the hair has much smoother surface after treatment with the sulfate-free cosmetic rinse-off composition as described above in great detail, as compared to the respective composition which does not comprise the hyperbranched copolymer of the monomers (i), (ii) and (iii).

In an even further aspect, the present invention relates to the use of a hyperbranched copolymer of the monomers
(i) dodecenyl succinic acid anhydride
(ii) diisopropanol amine
(iii) bis-dimethylaminopropyl amine
having terminal groups of formula

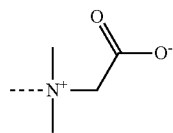

and having a molecular weight Mn of between 1200 and 4000 g/mol for increasing the curl definition of curled hair.

It has been observed that hair which is treated with a composition comprising said hyperbranched copolymer has a significant better curl definition as compared to the case where the respective composition does not comprise said hyperbranched copolymer. The term curl definition is known to the person skilled in the art.

In an even further aspect, the present invention relates to a method for treating hair or skin characterized in that it comprises the steps
α) applying a sulfate-free cosmetic rinse-off composition as described above in great detail to hair or skin;
β) rubbing the hair or skin to generate foam;
γ) rinsing the hair or skin with water.

Examples

The present invention is further illustrated by the following experiments. These examples are illustrative only and are not intended to limit the scope of the invention in any way.

Preparation of Hyperbranched Co Polymer (HBC1)

The hyperbranched copolymer HBC1 of the monomers dodecenyl succinic acid anhydride and diisopropanol amine and bis-dimethylaminopropyl amine has been prepared according to example 3 in EP 2 794 729 B1 using 237.59 g of N,N-bis(N'N'-dimethylaminopropyl)amine and 112.6 g diisopropanol amine and 426.89 g of dodecenylsuccinic anhydride. After heating and vacuum, the residual carboxylic acid content of <0.3 meq/g (tritrimetrical analysis) AV=9.8 mg KOH/g and amine content of 2.99 meq/g (tritrimetrical analysis) and a molecular weight Mn=2240 Da was obtained. This product has been reacted with sodium chloroacetate in water and stirred at 80° C. until 1H-NMR analysis shows a complete conversion of the chloroacetate to obtain the hyperbranched copolymer HBC1 which has terminal groups of the formula

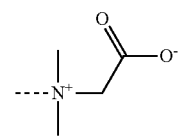

and a molecular weight Mn of 2.3 kDa.

The hyperbranched copolymer HBC1 was used as a 45 wt.-% solution in water in the following experiments.

Series of Experiment 1

Compositions

The sulphate-free shampoo compositions 1, 2, 3, 4, respectively Ref.1 and Ref.2 (without HBC1) have been prepared according to the amounts given in table 1.

TABLE 1

Shampoo compositions (numbers in % by weight).

| Ingredients | Ref. 1 | Ref. 2 | 1 | 2 | 3 | 4 |
|---|---|---|---|---|---|---|
| HBC1 (45%) | | | 1.0 | 2 | 1.66 | 3.33 |
| Polyquaternium 6 (35%) | | 2.3 | 2.3 | 2.3 | | |
| Hostapon CCG (Sodium cocoyl glutamate) | 10.0 | 10.0 | 10.0 | 10.0 | 10.0 | 10.0 |
| Dehyton AB-30 (Coco-betaine) | 10.0 | 10.0 | 10.0 | 10.0 | 10.0 | 10.0 |
| Proteol APL (Sodium Cocoyl Apple Amino acids) | 12.0 | 12.0 | 12.0 | 12.0 | 12.0 | 12.0 |

TABLE 1-continued

Shampoo compositions (numbers in % by weight).

| Ingredients | Ref. 1 | Ref. 2 | 1 | 2 | 3 | 4 |
|---|---|---|---|---|---|---|
| Pyridoxine hydrochloride | 0.25 | 0.25 | 0.25 | 0.25 | 0.25 | 0.25 |
| Betaine | 2.0 | 2.0 | 2.0 | 2.0 | 2.0 | 2.0 |
| Levenol H&B | 3.6 | 3.6 | 3.6 | 3.6 | 3.6 | 3.6 |
| Iricalmin ® PF | 2.0 | 2.0 | 2.0 | 2.0 | 2.0 | 2.0 |
| L-Lactic acid (90%) | 1.0 | 1. | 1.0 | 1.0 | 1.0 | 1.0 |
| Poly Suga Mulse D9 | 2.0 | 2.0 | 2.0 | 2.0 | 2.0 | 2.0 |
| Perfume | 0.5 | 0.5 | 0.5 | 0.5 | 0.5 | 0.5 |
| Sodium L-Lactate (60%) | 1.4 | 1.4 | 1.4 | 1.4 | 1.4 | 1.4 |
| Water | ad 100 | ad 100 | ad 100 | ad 100 | ad 100 | ad 100 |

Furthermore, a sulfate-containing shampoo of the following composition has been used (Ref.0).

TABLE 2

Sodium laureth sulfate(SLS) based shampoo composition (numbers in % by weight).

| Ingredients | Ref. 0 |
|---|---|
| Texapon NSO BZ (sodium laureth sulfate*) | 35.0 |
| Tego Betain F50 | 5.0 |
| Sodium Benzoate | 0.5 |
| Citric Acid | 0.15 |
| Water | ad 100 |

Measurement of Combing Force

Five hair swatches were used per test product (Kerling Art.826200 European hair, weight: 2.1-2.2 g, length 20 cm, free hair 18 cm, color 10/0 strong bleached, mix 810). 10 measurements were performed for each hair swatch.

The hair swatches have been washed with standard shampoo (10 seconds wetting, 30 seconds shampooing, 30 seconds rinsing) and dried overnight under defined conditions (21±1° C., 65% rH (rH=relative humidity).

For the dry combing: All swatches were directly measured.

For the wet combing: All swatches were pre-conditioned in warm water for 10 minutes and 30 seconds wetting (water 38° C.).

The combing force of the untreated dry, respectively wet (~60%) hair was measured using a tensile testing machine type INSTRON 4250.

The swatches are pulled through a fix comb (1 mm gap between combteeth) at a speed of 500 mm/min. The force measured is $F_0$.

After the measurement of the untreated hair, the swatches have been dried overnight under defined conditions (21±1° C., 65% rH).

Then the swatches were treated with the respective composition Ref.0, Ref.1, Ref.2, 1, 2, 3, or 4 (shampoo 0.25 ml/g hair), foamed for 30 seconds, rinsing for 30 seconds (water 38° C.).

For the dry combing: All swatches were dried overnight under defined conditions (21±1° C., 65% rH).

For the wet combing: All swatches were directly measured.

The combing force of the treated wet (~60%), respectively dry hair was measured the same way using a tensile testing machine type INSTRON 4250. The force measured is $F_1$.

In table 3, the relative improvement of combing force ($ICF_{rel}$) has been calculated according to the formula:

$$ICF_{rel} = \left(\frac{F_0 - F_1}{F_0}\right) * 100$$

Negative values of $ICF_{rel}$ indicate a decline in combability, whereas positive values indicate an improvement in the combability of the hair by the treatment.

TABLE 3

Improvement of combing (wet or dry hair)

| | Ref. 0 | Ref. 1 | Ref. 2 | 1 | 2 | 3 | 4 |
|---|---|---|---|---|---|---|---|
| Dry combing | | | | | | | |
| $ICF_{rel}$ | −4 | −23 | −94 | −20 | −12 | +14 | +5 |
| Wet combing | | | | | | | |
| $ICF_{rel}$ | −47 | +6 | +49 | +57 | +65 | +14 | +21 |

As one can see from the results of table 3, the sulfate-based shampoo (Ref.0) has only a very low decline in combability in the combing of dry hair, but has a significant decline of combability in combing wet hair. The sulfate-free reference shampoo (Ref.1) has only a slight improvement in combing of wet hair, but has a strong decline in combing of dry hair. When a cationic polymer having quaternary ammonium groups is added (Ref.2) the decline in combing dry hair is significantly increased, whereas the improvement in combing wet hair is significantly increased.

When the hyperbranched polymer is added to the sulfate-free reference shampoo (Ref.1) the combing both of dry and wet hair is significantly improved (3 and 4). When the hyperbranched polymer is added to the sulfate-free reference shampoo comprising the cationic polymer having quaternary ammonium groups (Ref.2), a negative effect of the cationic polymer for the combing of dry hair can be more than compensated, and the positive effect of the cationic polymer having quaternary ammonium groups in combing of wet hair is strongly enhanced by adding the hyperbranched polymer (1 and 2).

Hence the results table 3 show the surprising increase of combing property, particularly by significant lower combing forces in combing both dry and wet hair.

Curl Definition

Each hair swatch has been washed twice with the respective sulfate-free shampoo combination of table 1 (10 seconds wetting, 30 seconds shampooing, 30 seconds rinsing). Then each hair swatch has been rolled around a curler (12 mm diameter, plastic wire) (FIG. 1a) and dried overnight at 21° C., 65% rH).

Figure 1B:
Figure 1B:
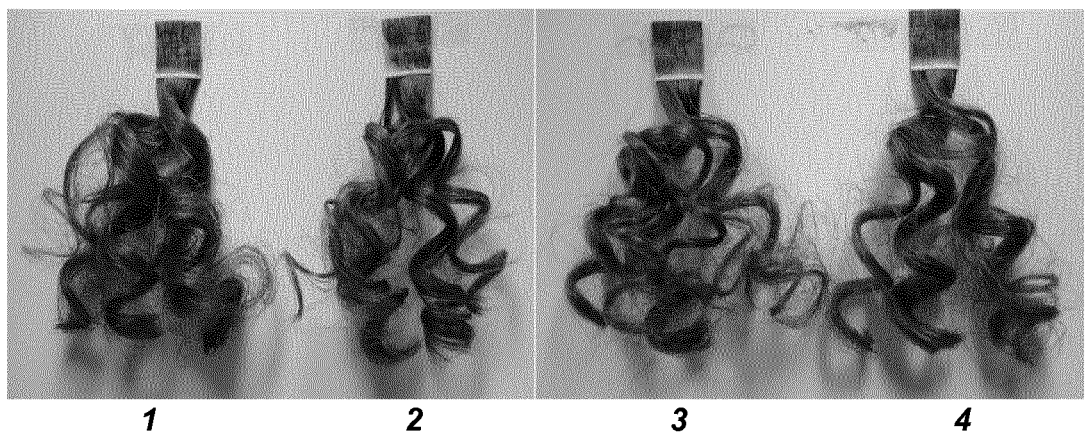

FIG. 1b shows photographs of the curls after the curling process described above.

What can be seen from FIG. 1b is that Ref.1 and Ref.2 have a very bad curl definition, whereas the examples 1, 2, 3 and 4 have a very nice curl definition.

Series of Experiment 2

The sulfate-free shampoo compositions 5, 6 respectively Ref.3 (without HBC1) have been prepared according to the amounts given in table 4.

TABLE 4

Shampoo compositions (numbers in % by weight).

| Ingredients | Ref. 3 | 5 | 6 |
|---|---|---|---|
| HBC1 (45%) | | 0.25 | 0.50 |
| Polyquaternium 22 (40%) | 1.25 | 1.25 | 1.25 |
| Hostapon CCG (Sodium cocoyl glutamate) | 10.00 | 10.00 | 10.00 |
| Dehyton AB-30 (Coco-betaine) | 10.00 | 10.00 | 10.00 |
| Proteol APL (Sodium Cocoyl Apple Amino acids) | 12.0 | 12.0 | 12.0 |
| Pyridoxine hydrochloride | 0.15 | 0.15 | 0.15 |
| Betaine | 2.0 | 2.0 | 2.0 |
| Pentavitin ® PF | 0.2 | 0.2 | 0.2 |
| Levenol H&B | 2.6 | 2.6 | 2.6 |
| L-Lactic acid (90%) | 1.0 | 1.0 | 1.0 |
| Poly Suga Mulse D9 | 1.4 | 1.4 | 1.4 |
| Perfume | 0.6 | 0.6 | 0.6 |
| Sodium L-Lactate (60%) | 1.4 | 1.4 | 1.4 |
| Colorant | 0.18 | 0.18 | 0.18 |
| Water | ad 100 | ad 100 | ad 100 |

Measurement of the Foam Development

The foam development of the shampoo compositions of table 4 has been measured by using a SITA foam tester R-2000 (SITA Messtechnik GmbH) (250 ml testing volume, stirrer 700 rpm, stirring time 10 seconds, temp. 23° C.).

Figure 2:
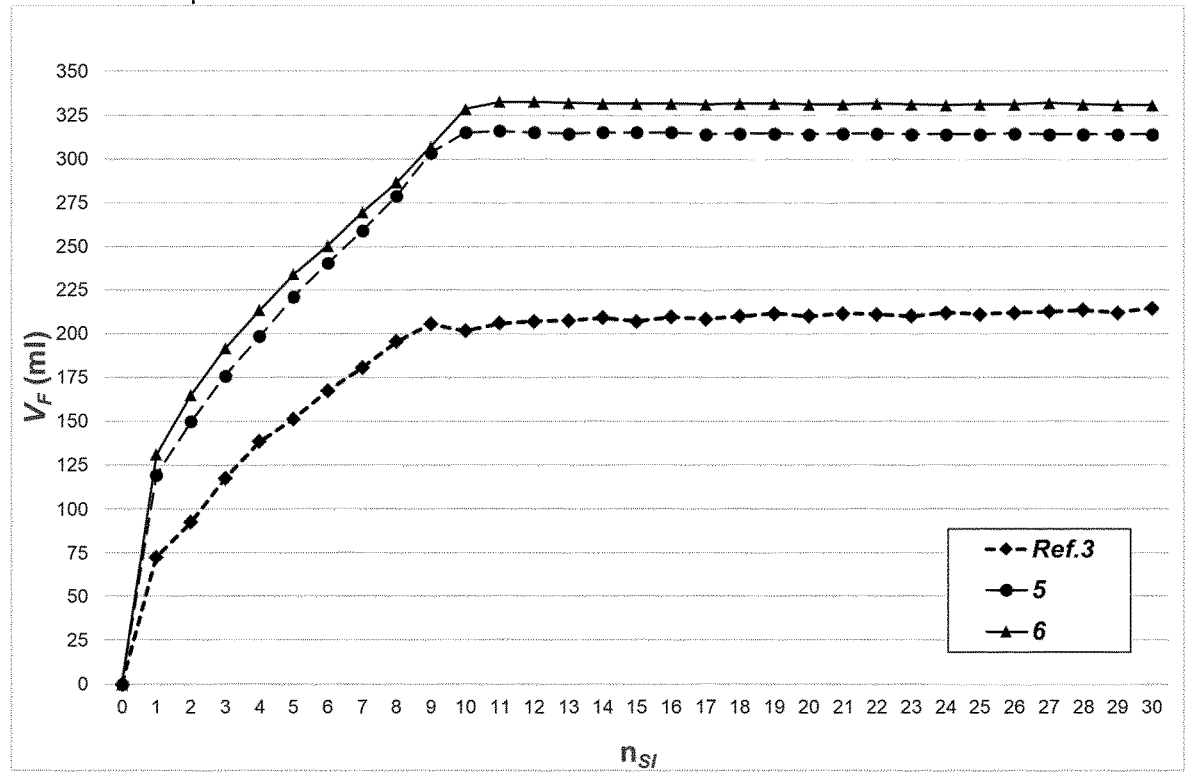

Foam is generated by means of a rotor and the volume of the foam produced is determined by determining the surface profile of the foam with the aid of a sensor module having a plurality of needle detectors. The foam volume $V_f$ has been measured after each of the stirring intervals $n_{SI}$ up to a total of 30 intervals. The values indicated in table 5 and FIG. 2 are the values obtained by averaging 2 measurements, total of 30 stirring intervals).

TABLE 5

Foam development.

| $n_{SI}$ | Ref. 3 $V_f$ [ml] | 5 $V_f$ [ml] | 6 $V_f$ [ml] |
|---|---|---|---|
| 0 | 0 | 0 | 0 |
| 5 | 151.5 | 221.0 | 234.0 |
| 10 | 201.5 | 315.0 | 328.5 |
| 15 | 207.0 | 315.0 | 331.5 |
| 20 | 210.0 | 314.0 | 331.0 |
| 25 | 211.0 | 314.0 | 331.0 |
| 30 | 214.5 | 314.0 | 330.5 |

In FIG. 2, the measured volume of foam $V_f$ has been plotted against the number of intervals $n_{SI}$.

The results of table 5, resp. FIG. 2, show that the maximal foam volume is about 215 ml for Ref.3, about 315 ml for 5 and about 331 ml for 6.

Measurement of the Foam Decay

The decay of foam has been measured by SITA foam tester R-2000 in monitoring the volume of foam ($V_{Ft}$) each 10 seconds during a period of 10 minutes (t) and compared with the initial foam volume ($V_0$). The relative foam volume (RFV) (=$V_{Ft}/V_0$) are indicated in table 6 and FIG. 3.

| t [s] | Ref. 3 RFE | 5 RFE | 6 RFE |
|---|---|---|---|
| 10 | 0.983 | 0.998 | 1.000 |
| 60 | 0.991 | 0.997 | 0.998 |
| 110 | 0.991 | 0.997 | 0.997 |
| 150 | 0.991 | 0.995 | 0.994 |
| 200 | 0.988 | 0.992 | 0.992 |
| 250 | 0.984 | 0.987 | 0.989 |
| 310 | 0.984 | 0.986 | 0.988 |
| 350 | 0.981 | 0.986 | 0.988 |
| 410 | 0.977 | 0.981 | 0.983 |
| 460 | 0.974 | 0.979 | 0.980 |
| 500 | 0.972 | 0.978 | 0.979 |
| 540 | 0.967 | 0.978 | 0.977 |
| 570 | 0.967 | 0.975 | 0.974 |

Figure 3:
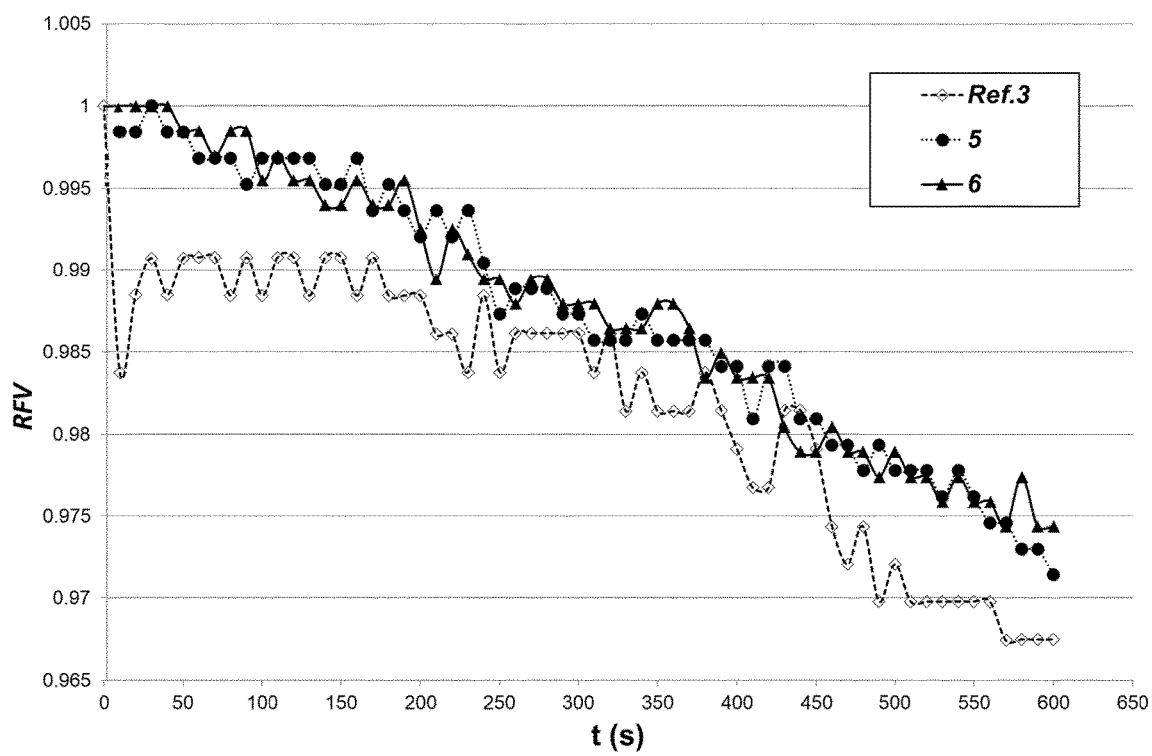

In FIG. 3, the relative foam volume (RFV) has been plotted as a function of time (t).

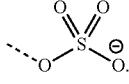

23. The method according to claim 21, wherein the sulfate-free cosmetic rinse-off composition comprises less than 0.05% by weight, relative to the weight of the composition, of any anionic surfactant having a terminal anionic group of the formula
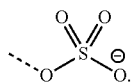

The invention claimed is:

1. A sulfate-free cosmetic rinse-off composition comprising:
   (a) a hyperbranched copolymer;
   (b) at least one cationic polymer having quaternary ammonium groups, and
   (c) an amphoteric surfactant which is acyl glutamate having an acyl group which comprises from 8 to 19 carbon atoms, wherein
   the hyperbranched copolymer is a copolymerization reaction product of the monomers:
     (i) dodecenyl succinic acid anhydride,
     (ii) diisopropanol amine, and
     (iii) bis-dimethylaminopropyl amine, and wherein
   the hyperbranched copolymer has terminal groups of the formula

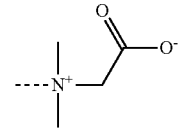

and has a molecular weight Mn of between 1200 and 4000 g/mol; and wherein
   the sulfate-free cosmetic rinse-off composition comprises less than 0.5% by weight, relative to the weight of the composition, of any anionic surfactant having a terminal anionic group of the formula

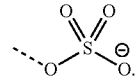

2. The sulfate-free cosmetic rinse-off composition according to claim 1, wherein the hyperbranched copolymer is prepared by the steps of:
   a1) polymerizing the monomers (i) and (ii) and (iii) to yield a polyesteramide having terminal dimethylamino groups of the formula

and
   a2) quaternization of the dimethyl amino groups of the polyesteramide of step a1) by 2-chloroacetate.

3. The sulfate-free cosmetic rinse-off composition according to claim 1, wherein a molar ratio of the monomer (i) to the monomer (ii) is between 5:1 and 0.5:1.

4. The sulfate-free cosmetic rinse-off composition according to claim 1, wherein a molar ratio of the monomer (i) to the monomer (iii) is between 5:1 and 0.5:1.

5. The sulfate-free cosmetic rinse-off composition according to claim 1, wherein the hyperbranched copolymer has a number average molecular weight Mn of between 1400 and 3000 g/mol.

6. The sulfate-free cosmetic rinse-off composition according to claim 1, wherein the hyperbranched copolymer is polyquaternium-110.

7. The sulfate-free cosmetic rinse-off composition according to claim 1, wherein the at least one cationic polymer having quaternary ammonium groups is either:

(i) a homopolymer (P1) of

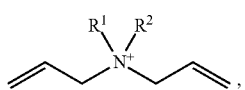

or (ii) a copolymer (P2) of

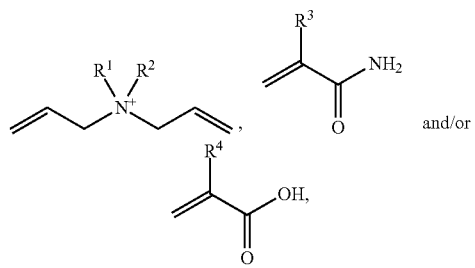

wherein
$R^1$ and $R^2$ represent independently from each other either a linear or a branched $C_{1-10}$-alkyl group, and
$R^3$ and $R^4$ represent independently from each other either H or a methyl group.

8. The sulfate-free cosmetic rinse-off composition according to claim 1, wherein the cationic polymer having quaternary ammonium groups is selected from the group consisting of polyquaternium-6, polyquaternium-7, polyquaternium-22 and polyquaternium-39.

9. The sulfate-free cosmetic rinse-off composition according to claim 1, wherein the cationic polymer having quaternary ammonium groups is a copolymer of vinylpyrrolidone having quaternary ammonium groups selected from the group consisting of polyquaternium-11, polyquaternium-16, polyquaternium-28, polyquaternium-44, polyquaternium-46, polyquaternium-68 and polyquaternium-87.

10. The sulfate-free cosmetic rinse-off composition according to claim 1, wherein the cationic polymer having quaternary ammonium groups is a hydroxyethyl cellulose derived polymer having quaternary ammonium groups selected from the group consisting of polyquaternium-4, polyquaternium-10, polyquaternium-24 and polyquaternium-67.

11. The sulfate-free cosmetic rinse-off composition according to claim 1, wherein the sulfate-free cosmetic rinse-off composition is a sulfate free shampoo composition.

12. The sulfate-free cosmetic rinse-off composition according to claim 1, which comprises less than 0.1% by weight, relative to the weight of the composition, of any anionic surfactant having the terminal anionic group of the formula

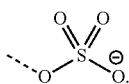

13. The sulfate-free cosmetic rinse-off composition according to claim 1, which comprises less than 0.05% by weight, relative to the weight of the composition, of any anionic surfactant having the terminal anionic group of the formula

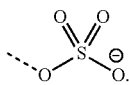

14. The sulfate-free cosmetic rinse-off composition according to claim 2, wherein step the dimethyl amino groups of the polyesteramide of step a1) is quaternized in step a2) by sodium 2-chloroacetate.

15. The sulfate-free cosmetic rinse-off composition according to claim 1, wherein the molar ratio of the monomer (i) to the monomer (ii) is between 4:1 and 1:1.

16. The sulfate-free cosmetic rinse-off composition according to claim 1, wherein the molar ratio of the monomer (i) to the monomer (ii) is between 3:1 and 3:2.

17. The sulfate-free cosmetic rinse-off composition according to claim 1, wherein the molar ratio of the monomer (i) to the monomer (iii) is between 3:1 and 1:1.

18. The sulfate-free cosmetic rinse-off composition according to claim 1, wherein the molar ratio of the monomer (i) to the monomer (iii) is between 2.5:1 and 1.1:1.

19. The sulfate-free cosmetic rinse-off composition according to claim 1, wherein the hyperbranched copolymer has a number average molecular weight Mn of between 2100 and 2400 g/mol.

20. The sulfate-free cosmetic rinse-off composition according to claim 7, wherein $R^1$ and $R^2$ represent independently from each other either a linear or branched $C_{1-3}$-alkyl group.

21. A method for treating hair or skin which comprises the steps of:
α) applying the sulfate-free cosmetic rinse-off composition according to claim 1 to hair or skin;
β) rubbing the hair or skin to generate foam; and
γ) rinsing the hair or skin with water.

22. The method according to claim 21, wherein the sulfate-free cosmetic rinse-off composition comprises less than 0.1% by weight, relative to the weight of the composition, of any anionic surfactant having a terminal anionic group of the formula